United States Patent [19]

Lee et al.

[11] Patent Number: 5,004,920

[45] Date of Patent: Apr. 2, 1991

[54] METHOD OF PREPARING MEMBRANE FILTERS FOR TRANSMISSION ELECTRON MICROSCOPY

[75] Inventors: Richard J. Lee, Murrysville; Barbara A. Smith, Apollo; Robert G. Theys, Monroeville; Robert A. Theys, Pittsburgh, all of Pa.; Judy A. Murphy, St. Louis, Mo.

[73] Assignee: RJ Lee Group, Inc., Monroeville, Pa.

[21] Appl. No.: 537,156

[22] Filed: Jun. 12, 1990

Related U.S. Application Data

[63] Continuation of Ser. No. 359,150, May 31, 1989, abandoned.

[51] Int. Cl.$^5$ .............................................. G01N 1/28
[52] U.S. Cl. .................................. 250/304; 250/307; 436/176; 436/178
[58] Field of Search ....................... 250/304, 307, 311; 436/178, 176

[56] References Cited

U.S. PATENT DOCUMENTS 2,875,341  2/1959  Nesh ................................. 250/49.5

FOREIGN PATENT DOCUMENTS 59-34132  2/1984  Japan .

OTHER PUBLICATIONS

Pattnaik et al, Scanning Electron Microscopy 11976 (Part III), Proceedings of the Workshop on Techniques for Particulate Matter Studies in SEM, Apr. 1976, pp. 441–450.

*The Journal of General Microbiology*, vol. 17, No. 1, Aug. 1957, pp. 75–79, "An Electron Microscope Study of the Spores of Some Species of the Genus Bacillus using Carbon Replicas", D. E. Bradley and D. J. Williams.

Industrial Lab. (U.S.A.), vol. 45, No. 3 (1979), "Rapid Aimed Preparation of Replicas (Exchange of Experience)", A. Kornienko and A. A. Nikolaenko.

*Primary Examiner*—Jack I. Berman
*Attorney, Agent, or Firm*—Webb, Burden, Ziesenheim & Webb

[57] ABSTRACT

This application relates to a method for preparing specimens for viewing particles and/or fibers captured upon membrane filters with a TEM. The method comprises mounting a section of the membrane filter on a glass slide with a quick drying liquid applied between the filter membrane and the slide which liquid will not release the filter membrane when the slide is immersed in a selected solvent and such that the liquid will not render the filter membrane resistant to the selected solvent. Next, the filter section surface is coated with carbon to replicate the surface of the membrane filter and the particles and fibers thereupon. The coated membrane is then immersed in the selected solvent which will attack the filter material causing the carbon film squares to float off of the memberane filter.

14 Claims, No Drawings

METHOD OF PREPARING MEMBRANE FILTERS FOR TRANSMISSION ELECTRON MICROSCOPY

This is a continuation of application Ser. No. 07/359,150, filed May 31, 1989 now abandoned.

BACKGROUND OF THE INVENTION

Transmission electron microscopy (TEM) is a known method of analyzing air filter samples for collected fibers and other particulates. Typically, the specimens are prepared for TEM by the Jaffe wick method in which membrane air filters (either of the polycarbonate or mixed cellulose ester type) containing collected particulate matter are first coated with carbon (on the particulate matter side) in a carbon evaporator. The carbon coated filter is then cut into small sections which are placed over the openings of a copper grid. The grid is placed horizontally on a sponge which is situated in a glass dish. An organic liquid which will dissolve the filter (chloroform for polycarbonate filters and acetone for mixed cellulose ester filters) is added to the dish until the liquid is level with the top surface of the sponge and thus in contact with the copper grid and the bottom surface of the filter. The liquid gradually dissolves the filter leaving behind the carbon film containing the particulate matter. The grid and carbon film can then be used as the specimen for the TEM analysis to determine the amount and nature of the particulate matter.

The Jaffe wick method is time consuming. In addition, the polycarbonate membrane filters do not always dissolve completely away, thus making the TEM image blurred and obscuring fibers and particles. Attempts to improve the Jaffe wick method, for example, by increasing the duration of the membrane dissolving step, simply have not resulted in an acceptable method.

TEM specimens have been prepared by floating of a carbon film from a substrate with particles entrapped. This technique has been used primarily to reproduce the structure of steel surfaces. The use of a carbon film on metal samples is described by Bradley and Williams, *J. Gen. Microbiology*, Vol. 17 (1957). However, it was not considered a technique for preparing specimens from soft and textured surfaces such as membrane filters.

Kornienko et al., Industrial Lab. (USA), Vol. 45, No. 3 (published September 1979) teaches a method for rapid preparation of replicas utilizing a celluloid film wetted in acetone and placed against the specimen. After drying, the film is detached from the specimen and a scratch on the surface of the specimen is clearly visible on the film. Subsequently, a platinum carbon replica is applied to the contact surface in a vacuum. The primary replica is then dissolved in acetone and the replica is recovered on a screen.

Japanese Publication 59-34132 teaches a method for preparation of a TEM replica sample in which Au, Pt or Pd is vapor-deposited on a polished surface by vacuum vapor-deposition.

U.S. Pat. No. 2,875,341 is of interest to show a method for preparation of replica specimens utilizing a coating of a plastic material such as polystyrene and benzol.

SUMMARY OF THE INVENTION

It is an advantage, according to this invention, to provide a faster specimen preparation method. Formerly, the Jaffe wick method, took a minimum of 24 hours from start to analysis time whereas with this method, the specimen can be ready for analysis within one hour.

It is a further advantage, according to this invention, that the specimen quality is far superior because the entire carbon film surface is exposed to the solvent. Formerly with the Jaffe wick method, some areas were blocked by the copper grid during dissolution.

It is yet another advantage, according to this invention, that less extensive reaction takes place between the solvent and the carbon film giving the film greater integrity.

It is still further an advantage, according to this invention, that TEM analysis time is shortened and the quality of the analysis is improved because the background is clearer, thus, there is less eye strain.

Briefly, according to this invention, there is provided a method of preparing a carbon replica specimen wherein the specimen replicates the surface of the membrane filter that has been used to capture fibers and other particles from air samples and most importantly, in turn, captures such fibers and particles and removes them from the filter for observation in the transmission electron microscope. The method comprises a first step of securing a section of the filter flat against a cover slip (glass slide). This step is essential for two reasons: it prevents the filter section from curling during further processing. It also holds the filter section allowing the carbon replica to be floated away in a later step. If the filter section is not secured as taught and claimed herein, the carbon replica will not release the filter section or the filter section will simply disintegrate when removal is attempted. The adhesive securing the filter to the slide must not tend to permeate and alter the solubility of the membrane filter making the filter itself (and especially the surface to be carbon coated) resistant to solvent. The selection and placement of the adhesive are thus critical. In one embodiment of this invention, it has been found that the adhesive should comprise a solution of lower alkyl alcohol soluble, glucose-based cyclolinear polyethers in a lower alkyl alcohol. The lower alkyl alcohol soluble, glucose-based cyclolinear polyethers may comprise, for example, methylcellulose, ethylhydroxyethylcellulose (EHEC), ethylcellulose, carboxylmethylcellulose, and hydroxypropyl methylcellulose. The lower alkyl alcohol solvent may comprise, for example, methyl alcohol, ethyl alcohol, 1-propyl alcohol, isopropyl alcohol, sec-butyl alcohol and tert-butyl alcohol. Other cellulose polymers and other polymers and stronger organic solvents may be substituted for the above, but for economic reasons, the lower alkyl alcohol soluble, glucose-based cyclolinear polyethers are preferred. An especially preferred adhesive comprises EHEC and isopropyl alcohol.

The adhesive may take the form of a solvent that attacks the membrane filter. In the case of polycarbonate membrane filters, the solvent may comprise chloroform or benzene, for example. Chloroform has been found to be especially preferred. In the case of mixed cellulose ester membrane filters, a suitable solvent is acetone.

The method according to this invention comprises a second step of vacuum evaporating a thin carbon film onto the membrane filter surface. In the case of mixed cellulose ester filters, an intermediate step precedes the carbon evaporation. The filters are treated to collapse or smooth the filter. The face of the filter that has collected the particulate specimen is replicated. The method comprises a third step of scoring tee carbon film, for example, in small squares to provide locations where solvent can penetrate the interface between the carbon film and the membrane filter. The fourth step comprises submerging the specimen in a solvent which will attack the membrane filter at the carbon filter interface, thus releasing the carbon film with the filtered fibers and particles attached thereto. The solvents described above as adhesives are also suitable for causing the release of the carbon film from the filter. The final step comprises capturing the carbon film replica on a TEM grid and drying. The specimen is then ready for TEM analysis.

DESCRIPTION OF THE PREFERRED EMBODIMENTS

The applicants invention will now be described with reference to working examples and several comparative tests.

EXAMPLE I (POLYCARBONATE FILTER)

A section of polycarbonate filter used for air sampling was mounted securely to a glass slide with the filtered particle side up. The filter was mounted using a thin layer of a 4% solution of ethylcellulose in isopropyl alcohol between the filter and glass slide. The assembly was allowed to dry completely in approximately 5 minutes. After drying, a thin film of carbon was vacuum evaporated using known techniques onto the surface of the filter section. The carbon film was then scored into about 2×2 mm squares and the assembly was placed in a dish of chloroform. As the chloroform attacked or dissolved away the filter at the carbon filter interface, the edges of the squares were tickled, thus causing the carbon film to float free. The carbon film contained all the fibers and other particles that had been on the surface of the filter after air sampling. The carbon film squares were then captured on a copper TEM grid and briefly dried. The samples were then ready for TEM analysis.

In a variation of this example, "liquid graphite", which has a carrier comprising ethylcellulose and isopropanol, was used to secure the membrane filter section to the slide; in this case the drying time had to be increased to about 15 minutes.

EXAMPLE II (POLYCARBONATE FILTERS)

This example was substantially identical to Example I except that in place of the ethylcellulose and isopropanol, 1 to 2 microliter droplets of chloroform were placed at several points on the edges of the filter section to secure it to the slide.

The chloroform apparently attacks the filter at the interface between the filter and the slide thus causing it to be adhesively bonded to the slide but, because of the controlled small amount of chloroform used, does not alter the character of the remainder of the filter.

EXAMPLE III (MIXED CELLULOSE ESTER FILTERS)

A section of mixed cellulose ester filter was used for sampling and was thereafter mounted securely to a glass slide, filtered particle side up. The filter was mounted to the slide using a thin layer of a 1% solution of EHEC in isopropanol between the filter and the glass slide. It was allowed to dry completely in approximately 20 minutes. The assembly was then treated in acetone vapor and given a low temperature plasma etching treatment to collapse and smooth the filter surface. A thin film of carbon was vacuum evaporated upon the surface of the filter section. The filter was treated in an atmosphere of acetone vapor and then given a low temperature plasma etch. The acetone vapor and plasma etch steps collapse or relax the complex filter structure and provide a smooth background to simplify viewing the sample. These steps are done in accordance with the procedures recommended by AHERA. The carbon layer was then scored into 2×2 mm squares and the assembly was placed in a dish of acetone. As the acetone attacked or dissolved away the filter at the filter carbon film interface, the edges of the squares were tickled, thus causing the carbon film to float free. The carbon film contained all the fibers and other particles that had been on the surface of the filter after air sampling. The carbon film squares were then captured on a copper TEM grid and briefly dried. The samples were ready for TEM analysis.

In a variation of this example, "liquid graphite" was used to secure the filter to the slide.

EXAMPLE IV (MIXED CELLULOSE ESTER FILTERS)

Example IV is substantially identical to Example III except that in place of the ethylcellulose in isopropanol, 1 to 2 microliter droplets of acetone were placed at several points on the edge of the filter section securing it to the membrane. The acetone apparently attacks the filter at the interface between the filter and the slide thus causing it to be adhesively bonded to the slide, but because of the controlled small amount of acetone used, does not alter the character of the remainder of the filter.

COMPARATIVE TESTS

Prior to the discoveries disclosed and claimed herein, applicants tried a number of methods of securely attaching the filter section to the glass slide. In a procedure similar to Example I, the polycarbonate filter specimen was secured by epoxy cement. When placed in chloroform, the carbon film, with considerable filter still attached, lifted off the slide in large pieces and would not adhere to the copper TEM grids. Also edges did not remain flat but curled upon drying. Apparently the epoxy was absorbed into the filter, thus, preventing the filter from being dissolved so that the carbon film could float free. In another procedure similar to Example I, the specimen was secured with Balsam or Duco cement. When placed in chloroform, both filter and carbon lifted off very quickly and broke up into small unusable pieces. In yet another procedure similar to Example I, the sample was secured with double sided adhesive tape. The adhesive remained viscid and appeared to be absorbed into the filter causing problems similar to those caused by the epoxy cement. In still yet another procedure similar to Example I, Scotch tape was used to hold down edges of filter section. When placed in chloroform, the carbon film sections were very difficult to retrieve and would stick to the bottom of the dish.

Because it appeared that normal adhesives would not work, a completely different type of material was tried. A commercially produced material called liquid graphite (colloidal graphite, suspended in an organic fluid such as isopropanol), which is commonly used because of its electrical conductivity to mount materials such as metallic samples and filters on stubs for examination in scanning electron microscopes was tried. Although its electrical conducting properties were not needed in the method being developed, it was decided to try the liquid graphite on the chance that it would satisfactorily secure the filter section to the glass slide during subsequent processing. The results of experiments (see Example I herein) using the liquid graphite were exceptionally good. The liquid graphite dried relatively rapidly in about 15 minutes and when placed in the chloroform, the carbon film containing the particles and fibers floated cleanly off the filter and could be readily collected for TEM examination.

The reason why the "liquid graphite" acts as an adhesive which securely attaches the filter to the glass slide while not hampering release of the carbon film was not known. However, it was concluded that the organic fluid used must not readily dissolve or attack the filter material. Liquid graphite made with base fluids other than isopropanol, such as butanol and methanol, were also investigated and found to also work satisfactorily although isopropanol was found to work best because it provides the optimum drying time—not too fast or too slow.

A chemical analysis of the "liquid graphite" showed that it also contained ethylcellulose or ethyl hydroxyethyl cellulose (EHEC) polymers in relatively small amounts. Therefore, experiments were conducted with various solutions of isopropanol and an EHEC polymer. It was found that solutions containing about 0.2% to 15% for cellulose ester filters and 1% to 15% for polycarbonate filters of EHEC in isopropanol worked as well as the "liquid graphite", and it became apparent that an organic solution containing, as a base, chemicals such as isopropanol which will not dissolve the filter plus about 1 to 15% of a polymer such as EHEC would work satisfactorily. It is hypothesized that the polymer is the material which performs the function of attaching the filter to the glass slide with the isopropanol acting as a carrier solvent which evaporates leaving behind the polymer to act as an adhesive.

After the liquid graphite was used in the preparation of TEM samples from polycarbonate filters, it was also tried with cellulose ester filters. (See Example III herein). When mixed cellulose ester filters are used, additional preparation steps are necessary. After the filter section is attached to the glass slide, it is treated in acetone vapor and then given a low temperature plasma etching treatment to collapse or smooth the filter surface. These additional steps had no effect on the effectiveness of the liquid graphite in providing a secure attachment of the filters to the glass slide and in the subsequent "clean" release of the carbon film containing particles and fibers from the filter.

Another method of securely attaching the filter to the glass slide was also tried. With this method the filter section was placed on the glass slide and small droplets of an organic solvent which will tend to dissolve the filter material were placed at appropriate points around the edge of the filter. Chloroform was used for polycarbonate filters and acetone was used for mixed cellulose ester filters. (See Example II and IV herein). After some experimentation, it was found that if the proper amount of solvent is applied at several spots around the filter edge, it will flow between the slide and filter due to capillary action and cause the filter to be adhesively bonded to the slide. If too little solvent is used, inadequate bonding is achieved; if too much is used, excessive dissolution of the filter occurs. It was established that the placement of about 1 to 2 microliters of solvent at each of two locations was highly satisfactory. Filters prepared in this way were readily processed through the subsequent steps required, as discussed above, for the preparation of samples for TEM analysis.

Experiments were also conducted on the scoring of the filter to establish the optimum size of the scored squares. These studies showed that 2 to 2 mm squares provided optimum lift-off of the carbon film and an appropriate size for capture on the copper grids. Squares in the range of 0.5 to 5 mm are also satisfactory.

As a result of these experiments, a new method has been developed to prepare membrane filters for TEM examination. This sample preparation method is applicable to both polycarbonate and mixed cellulose ester filters and its simplicity makes it suitable for routine use in preparing samples for TEM analysis.

Subsequent to its development, applicants put the basic method into use, but continued to refine the techniques for capturing the floating carbon film and to determine the optimum film thickness which was about 400 angstroms.

Applicants also conducted studies to compare the results of analyses of specimens made with the method according to this invention and the Jaffe wick method. Unexpectedly, applicants recognized that the levels of asbestos fibers that were encountered in blank quality-control polycarbonate filters (that is filters through which air had not passed) was generally lower than the levels reported by other laboratories which were using the Jaffe wick method for their sample preparation. Apparently, as a result of floating the carbon film from the filter by means of the new method, the film contains only those particles that were trapped on the filter surface itself during air sampling. On the other hand, the carbon film from the Jaffe wick method not only contains those fibers and particles resident on the surface of the filter but also fiber contamination that may be part of the filter material itself.

Historically, polycarbonate filters have presented contamination problems to many laboratories. They have an average blank level of asbestos fibers considerably higher than applicants experience with this new method. This presents major problems when post abatement fiber concentration is critical and the presence of a single asbestos fiber could cause the sample to exceed allowable limits.

Having thus described our invention with the detail and particularity required by the Patent Laws, what is claimed and desired protected by Letters Patent is set forth in the following claims.

We claim:

1. The method for preparing specimens for viewing particles and/or fibers captured upon membrane filters with a TEM comprising the following steps:
   (a) mounting a section of the membrane filter on a glass slide with a quick drying liquid applied between the filter membrane and the slide which liquid will not release the filter membrane when the slide is immersed in a selected solvent and such that the liquid will not render the filter membrane resistant to the selected solvent, the face of the membrane filter that has collected the particles and/or fibers to be observed facing away from the glass slide,
   (b) drying the assembly,
   (c) vacuum coating the filter section surface with carbon to replicate the surface of the membrane filter and the particles and fibers thereupon, (d) scoring the carbon coated membrane filter section into small sections, (e) immersing the assembly in the selected solvent which will attack the filter material causing the carbon film squares to float off of the membrane filter, and (f) capturing the film squares for use as transmission electron microscope specimens.

2. The method according to claim 1 wherein the quick drying liquid is a solution of lower alkyl alcohol soluble, glucose-based cyclolinear polyethers in lower alkyl alcohol.

3. The method according to claim 2 wherein the polyether is selected from the group consisting of methylcellulose, ethylhydroxyethylcellulose, ethylcellulose, carboxymethylcellulose and hydroxypropyl methylcellulose.

4. The method according to claim 2 wherein the alcohol solvent is selected from the group consisting of methyl, ethyl, propyl, and butyl alcohol.

5. The method according to claim 1 wherein the membrane filter is comprised of a polycarbonate film and the selected solvent is selected from the group consisting of chloroform and benzene.

6. The method according to claim 1 wherein the membrane filter is comprised of a mixed cellulose ester and the selected solvent is acetone.

7. The method according to claim 6 wherein after step (a) and prior to step (c) the assembly is treated to collapse and smooth the filter surface.

8. The method according to claim 1 wherein the quick drying liquid is a solvent that attacks the membrane filter.

9. The method according to claim 8 wherein the membrane filter is comprised of a polycarbonate film and the quick drying liquid is selected from the group consisting of chloroform and benzene.

10. The method according to claim 8 wherein the membrane filter is comprised of a mixed cellulose ester and the quick drying liquid is selected from the group consisting of acetone, chloroform, benzene and carbon tetrachloride.

11. The method according to claim 9 wherein 1 to 2 microliter droplets of quick drying liquids are placed at several locations along the edges of the filter section to secure it to the slide.

12. The method according to claim 10 wherein 1 to 2 microliter droplets of quick drying liquids are placed at several locations along the edges of the filter section to secure it to the slide.

13. The method according to claim 8 wherein the amount of quick drying liquid used to secure the filter to the slide is enough to attack the interface between the filter and the slide but not enough to alter the character of the remainder of the filter.

14. The method for preparing specimens for viewing particles and/or fibers captured upon membrane filters comprising the following steps:

(a) mounting a section of the membrane filter on a slide with a drying liquid applied between the filter membrane and the slide which liquid will not release the filter membrane when the slide is immersed in a selected solvent and such that the liquid will not render the filter membrane resistant to the selected solvent, the face of the membrane filter that has collected the particles and/or fibers to be observed facing away from the slide, (b) drying the assembly, (c) vacuum coating the filter section surface with carbon to replicate the surface of the membrane filter and the particles and/or fibers thereupon, (d) scoring the carbon coated membrane filter section into small sections, (e) immersing the assembly in the selected solvent which will attack the filter material causing the carbon film squares to float off of the membrane filter, and (f) capturing the film squares for use as specimens.

* * * * *